(12) United States Patent
Tanigami et al.

(10) Patent No.: US 12,226,082 B2
(45) Date of Patent: Feb. 18, 2025

(54) MEDICAL SYSTEM, ENERGY CONTROL METHOD, AND PROCESSOR

(71) Applicant: OLYMPUS CORPORATION, Hachioji (JP)

(72) Inventors: Yasuo Tanigami, Tokyo (JP); Yusuke Otsuka, Yokohama (JP); Noriko Kuroda, Machida (JP); Yuji Kishimoto, Kodaira (JP); Hideyuki Kasahara, Hamura (JP); Kazue Tanaka, Sagamihara (JP); Kunihide Kaji, Hachioji (JP); Satoshi Takekoshi, Hachioji (JP); Yoshitaka Honda, Hachioji (JP); Takaaki Igarashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 769 days.

(21) Appl. No.: 17/461,446

(22) Filed: Aug. 30, 2021

(65) Prior Publication Data

US 2021/0386270 A1 Dec. 16, 2021

Related U.S. Application Data

(63) Continuation-in-part of application No. PCT/JP2019/007864, filed on Feb. 28, 2019.

(51) Int. Cl.
*A61B 1/04* (2006.01)
*A61B 1/00* (2006.01)
*A61B 1/06* (2006.01)

(52) U.S. Cl.
CPC .......... *A61B 1/043* (2013.01); *A61B 1/00006* (2013.01); *A61B 1/000094* (2022.02);
(Continued)

(58) Field of Classification Search
CPC ... A61B 1/043; A61B 1/00094; A61B 1/0655; A61B 1/00006; A61B 1/0005;
(Continued)

(56) References Cited

U.S. PATENT DOCUMENTS

| 2010/0179522 A1* | 7/2010 | Companion ........... A61B 8/085 606/10 |
|---|---|---|
| 2013/0079645 A1 | 3/2013 | Amirana et al. |

(Continued)

FOREIGN PATENT DOCUMENTS

| CN | 108135475 A | 6/2018 |
|---|---|---|
| CN | 109171998 A | 1/2019 |

(Continued)

OTHER PUBLICATIONS

May 7, 2019 International Search Report issued in International Patent Application No. PCT/JP2019/007864.
(Continued)

*Primary Examiner* — John P Leubecker
(74) *Attorney, Agent, or Firm* — Oliff PLC

(57) ABSTRACT

A medical system can include a light source configured to generate excitation light; and a processor including a memory, the processor: controlling energy supplied to an energy device, the light source generating the excitation light to generate fluorescence from the living body tissue heat treated by the energy device; generating a fluorescence image based on an image pickup signal obtained by imaging the living body tissue; and generating a control signal that restricts energy supply to the energy device and output the control signal to the energy control apparatus when a pixel value of at least one pixel in the fluorescence image exceeds a first threshold value.

27 Claims, 8 Drawing Sheets

(52) U.S. Cl.
CPC ........ *A61B 1/0005* (2013.01); *A61B 1/00163* (2013.01); *A61B 1/0638* (2013.01); *A61B 1/0655* (2022.02)

(58) Field of Classification Search
CPC .............. A61B 1/00168; A61B 1/0638; A61B 1/00095; A61B 2018/00982
See application file for complete search history.

(56) References Cited

U.S. PATENT DOCUMENTS

| | | | |
|---|---|---|---|
| 2013/0102862 A1 | 4/2013 | Mercader et al. | |
| 2013/0190742 A1* | 7/2013 | Connors | A61B 18/20 606/17 |
| 2015/0141847 A1* | 5/2015 | Sarvazyan | A61B 5/0036 600/478 |
| 2015/0164332 A1 | 6/2015 | Mercader et al. | |
| 2015/0202005 A1* | 7/2015 | Fuflyigin | A61B 18/20 606/12 |
| 2015/0327753 A1 | 11/2015 | Amirana et al. | |
| 2016/0095661 A1* | 4/2016 | Rephaeli | A61B 5/0071 606/3 |
| 2016/0120599 A1* | 5/2016 | Amirana | A61B 5/0036 606/34 |
| 2017/0014202 A1 | 1/2017 | Ransbury et al. | |
| 2017/0354357 A1 | 12/2017 | Laughner et al. | |
| 2018/0263476 A1 | 9/2018 | Amirana et al. | |
| 2020/0121376 A1 | 4/2020 | Zhang et al. | |
| 2020/0261170 A1* | 8/2020 | Ziso | A61B 17/3403 |
| 2020/0367818 A1* | 11/2020 | DaCosta | A61K 41/0061 |
| 2021/0045834 A1 | 2/2021 | Ransbury et al. | |
| 2022/0095903 A1* | 3/2022 | McDowall | G16H 20/40 |

FOREIGN PATENT DOCUMENTS

| | | |
|---|---|---|
| CN | 109310333 A | 2/2019 |
| JP | 2012-183216 A | 9/2012 |
| JP | 2015-505678 A | 2/2015 |
| JP | 2016-127993 A | 7/2016 |
| JP | 2017-023604 A | 2/2017 |
| JP | 2018-075385 A | 5/2018 |
| JP | 2018-512911 A | 5/2018 |
| WO | 2013-044182 A1 | 3/2013 |
| WO | 2018/047369 A1 | 3/2018 |
| WO | 2020/053933 A1 | 3/2020 |
| WO | 2020/054723 A1 | 3/2020 |

OTHER PUBLICATIONS

May 10, 2024 Office Action issued in Chinese Patent Application No. 201980091476.1.

* cited by examiner

MEDICAL SYSTEM, ENERGY CONTROL METHOD, AND PROCESSOR

CROSS REFERENCE TO RELATED APPLICATION

This application is a continuation-in-part application of PCT/JP2019/007864 filed on Feb. 28, 2019, the entire contents of which are incorporated herein by this reference.

BACKGROUND OF THE INVENTION

1. Field of the Invention

The present invention relates to a medical system used to perform treatment on living body tissue under endoscopic observation, an energy control method, and a processor.

2. Description of the Related Art

In a medical field, a method of performing treatment on desired living body tissue by using an energy device such as an electrocautery scalpel has been conventionally known. For example, Japanese Patent Application Laid-Open Publication No. 2018-075385 discloses a configuration that is thought to be usable for the above-described treatment.

Specifically, Japanese Patent Application Laid-Open Publication No. 2018-075385 discloses a configuration including an endoscope and a catheter in which a conductor is covered by a ferromagnetic body, the configuration being used to perform treatment on tissue such as a tumor cell by applying energy through the catheter to generate heat from the tissue.

SUMMARY

A medical system according to exemplary embodiments can include a light source configured to generate excitation light; and a processor including a memory, the processor being configured to: control energy supplied to an energy device configured to perform heat treatment on living body tissue, the light source being configured to generate the excitation light to generate fluorescence from the living body tissue heat treated by the energy device; generate a fluorescence image based on an image pickup signal obtained by imaging the living body tissue irradiated with the excitation light; and generate a control signal configured to restrict energy supply to the energy device and output the control signal to the energy control apparatus when a pixel value of at least one pixel among a plurality of pixels included in the fluorescence image exceeds a first threshold value.

An energy control method according to exemplary embodiments can include generating a fluorescence image based on an image pickup signal obtained by imaging living body tissue irradiated with excitation light; and generating a control signal for restricting energy supply to an energy device and outputting the control signal to the energy control apparatus when a pixel value of at least one pixel among a plurality of pixels included in the fluorescence image exceeds a first threshold value.

A processor according to exemplary embodiments can include a processing circuit. The processing circuit is configured to: generate a fluorescence image based on an image pickup signal obtained by imaging living body tissue irradiated with excitation light; and generate a control signal configured to restrict energy supply to an energy device and output the control signal to an energy control apparatus, when a pixel value of at least one pixel among a plurality of pixels included in the fluorescence image exceeds a first threshold value.

DETAILED DESCRIPTION OF THE PREFERRED EMBODIMENT(S)

An embodiment of the present invention will be described below with reference to the accompanying drawings.

FIGS. 1 to 6 relate to the embodiment of the present invention.

Figure 1:
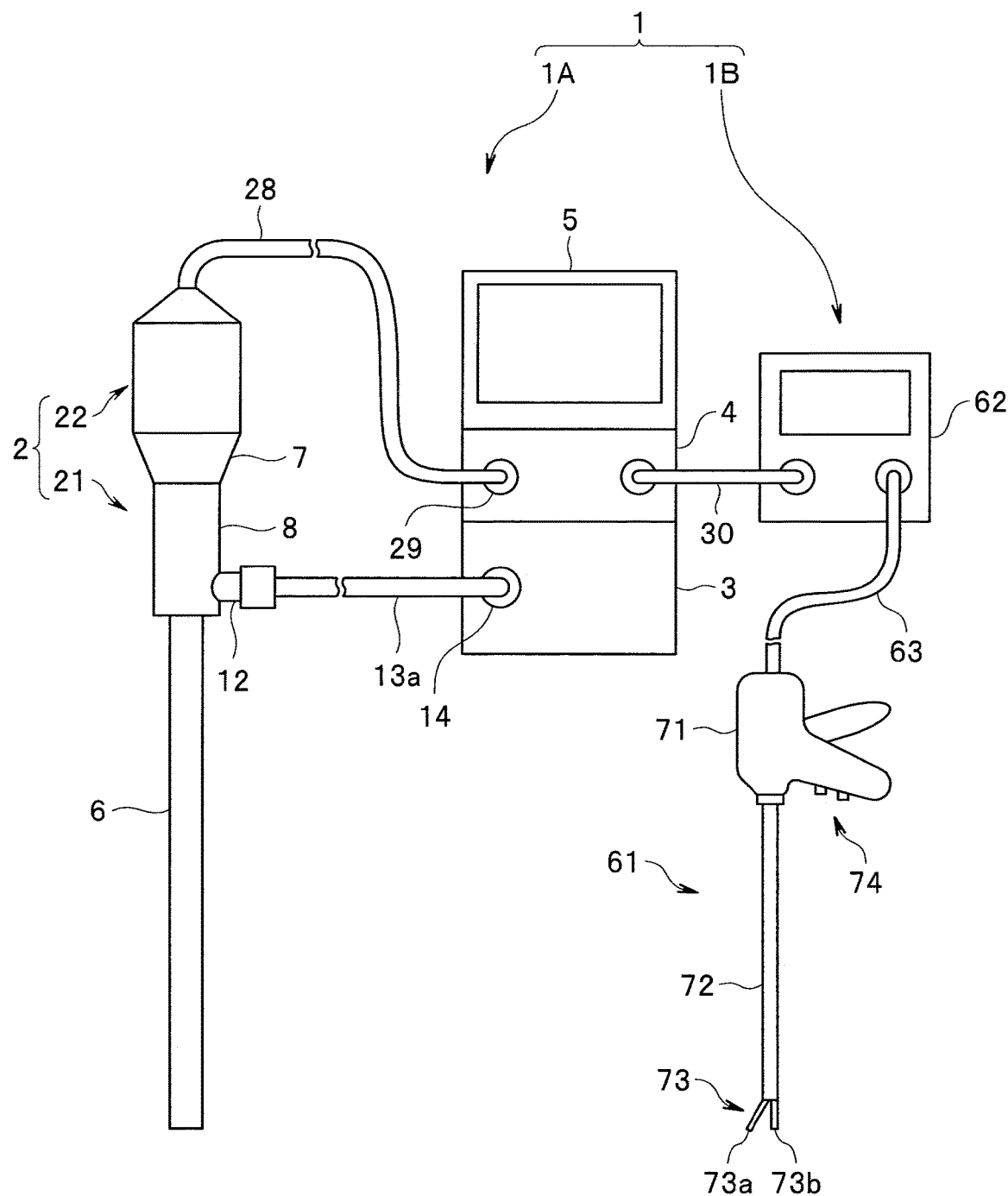
FIG. 1 is a diagram illustrating a configuration of a main part of a medical system according to an exemplary embodiment.

As illustrated in FIG. 1, a medical system 1 includes an endoscope system 1A used for observation of a desired object such as living body tissue present in a subject, and a treatment system 1B used for treatment on a desired treatment target site including the living body tissue present in the subject. The endoscope system 1A and the treatment system 1B are connected with each other through a signal cable 30. FIG. 1 is a diagram illustrating a configuration of a main part of the medical system according to the embodiment.

As illustrated in FIG. 1, the endoscope system 1A includes an endoscope apparatus 2, a light source apparatus 3, a processor 4, and a display apparatus 5, the endoscope apparatus 2 being inserted into the subject and configured to output an image obtained by performing image pickup of an object such as the living body tissue present in the subject, the light source apparatus 3 being configured to supply, to the endoscope apparatus 2, light with which the object is to be irradiated, the processor 4 being configured to generate a display image by performing predetermined image processing on the image outputted from the endoscope apparatus 2 and output the display image, the display apparatus 5 being configured to display the display image outputted from the processor 4 or the like on a screen. As illustrated in FIG. 1, the treatment system 1B includes a treatment instrument 61 and a treatment instrument control apparatus 62, the treatment instrument 61 being inserted into the subject and configured to perform treatment by applying energy to the living body tissue at the treatment target site present in the subject, the treatment instrument control apparatus 62 being configured to supply, to the treatment instrument 61, energy to be applied to the living body tissue at the treatment target site.

The endoscope apparatus 2 includes an optical viewing tube 21 and a camera unit 22, the optical viewing tube 21 including an elongated insertion portion 6, the camera unit 22 being detachably attached to an eye piece 7 of the optical viewing tube 21.

The optical viewing tube 21 includes the elongated insertion portion 6 that can be inserted into the subject, a grasping portion 8 provided at a proximal end portion of the insertion portion 6, and the eye piece 7 provided at a proximal end portion of the grasping portion 8.

Figure 2:
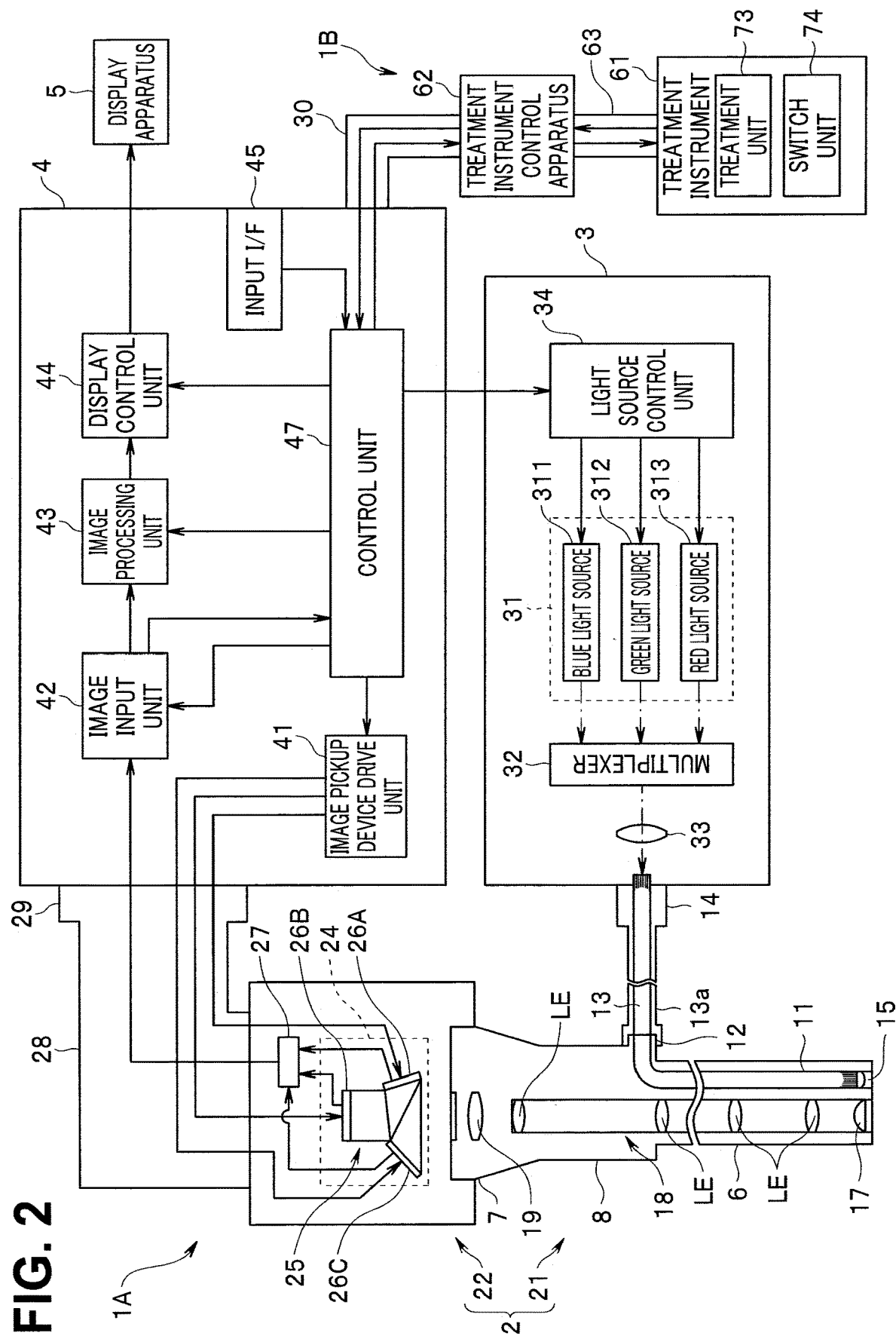
FIG. 2 is a diagram for describing an example of specific configurations of an endoscope system and a treatment system according to an exemplary embodiment.

As illustrated in FIG. 2, a light guide 11 for transmitting light supplied through a cable 13a is inserted inside the insertion portion 6. FIG. 2 is a diagram for describing an example of specific configurations of the endoscope system and the treatment system according to the embodiment.

As illustrated in FIG. 2, an emission end part of the light guide 11 is disposed near an illumination lens 15 at a distal end portion of the insertion portion 6. An incident end part of the light guide 11 is disposed in a light guide pipe sleeve 12 provided to the grasping portion 8.

As illustrated in FIG. 2, a light guide 13 for transmitting light supplied from the light source apparatus 3 is inserted inside the cable 13a. A connection member (not illustrated) detachably attached to the light guide pipe sleeve 12 is provided at one end part of the cable 13a. A light guide connector 14 detachably attached to the light source apparatus 3 is provided at the other end part of the cable 13a.

The illumination lens 15 for emitting, to outside, light transmitted by the light guide 11, and an objective lens 17 for obtaining an optical image in accordance with light incident from the outside are provided at the distal end portion of the insertion portion 6. An illumination window (not illustrated) at which the illumination lens 15 is disposed and an observation window (not illustrated) at which the objective lens 17 is disposed are provided adjacent to each other on a distal end surface of the insertion portion 6.

As illustrated in FIG. 2, a relay lens 18 including a plurality of lenses LE for transmitting the optical image obtained through the objective lens 17 to the eye piece 7 is provided inside the insertion portion 6. In other words, the relay lens 18 functions as a transmission optical system configured to transmit light incident through the objective lens 17.

As illustrated in FIG. 2, an eyepiece lens 19 through which the optical image transmitted through the relay lens 18 can be observed by a bare eye is provided inside the eye piece 7.

The camera unit 22 includes an image pickup unit 24 and a signal processing circuit 27.

The image pickup unit 24 includes a dichroic prism 25 and image pickup devices 26A, 26B, and 26C.

The dichroic prism 25 is configured as a spectroscopic element that separates light emitted through the eyepiece lens 19 into light of three wavelength bands, namely, light in a red region, light in a green region, and light in a blue region and emits each light.

The image pickup device 26A is configured by an image sensor such as a monochrome CCD. The image pickup device 26A is configured to perform image pickup operation in accordance with an image pickup device drive signal outputted from the processor 4. The image pickup device 26A is also configured to pick up light in the red region emitted through the dichroic prism 25 and generate and output an image pickup signal in accordance with the picked-up light in the red region.

The image pickup device 26B is configured by an image sensor such as a monochrome CCD. The image pickup device 26B is also configured to perform image pickup operation in accordance with an image pickup device drive signal outputted from the processor 4. The image pickup device 26B is also configured to pick up light in the green region emitted through the dichroic prism 25 and generate and output an image pickup signal in accordance with the picked-up light in the green region.

The image pickup device 26C is configured by an image sensor such as a monochrome CCD. The image pickup device 26C is also configured to perform image pickup operation in accordance with an image pickup device drive signal outputted from the processor 4. The image pickup device 26C is also configured to pick up light in the blue region emitted through the dichroic prism 25 and generate and output an image pickup signal in accordance with the picked-up light in the blue region.

In other words, the image pickup unit 24 is configured to be able to separate light emitted through the eyepiece lens 19 into light of three wavelength bands, namely, light in the red region, light in the green region, and light in the blue region and pick up each light.

The signal processing circuit 27 is configured to generate an image by performing predetermined signal processing such as correlated double sampling processing or A/D conversion processing on the image pickup signals outputted from the image pickup devices 26A, 26B, and 26C, and is configured to output the generated image to the processor 4 connected with a signal cable 28.

The light source apparatus 3 is configured to be able to generate excitation light for generating fluorescence from the living body tissue on which treatment is performed by the treatment instrument 61. The light source apparatus 3 includes a light emission unit 31, a multiplexer 32, a light condensation lens 33, and a light source control unit 34.

The light emission unit 31 includes a blue light source 311, a green light source 312, and a red light source 313.

The blue light source 311 includes a light emission element such as a blue LED. The blue light source 311 is configured to generate blue light (hereinafter referred to as B light) having intensity in the blue region and intensity in a wavelength band with which autofluorescence (hereinafter referred to as F light) in the green region can be generated from a fluorescence material as a generation source of autofluorescence at the living body tissue. Specifically, the blue light source 311 is configured to generate, for example, the B light having intensity in a wavelength band of 390 nm to 470 nm. The blue light source 311 is also configured to start or stop light emission in accordance with a light source drive signal supplied from the light source control unit 34. The blue light source 311 is also configured to perform light emission at light emission quantity in accordance with the light source drive signal supplied from the light source control unit 34.

The green light source 312 includes a light emission element such as a green LED. The green light source 312 is configured to generate green light (hereinafter referred to as G light) having intensity in the green region and intensity in a wavelength band for which an absorption coefficient for blood hemoglobin (composite of oxidized hemoglobin and reduced hemoglobin) is relatively high. Specifically, the green light source 312 is configured to generate, for example, the G light having intensity in a wavelength band of 540 nm to 560 nm. The green light source 312 is also configured to start or stop light emission in accordance with a light source drive signal supplied from the light source control unit 34. The green light source 312 is also configured to perform light emission at light emission quantity in accordance with the light source drive signal supplied from the light source control unit 34.

The red light source 313 includes a light emission element such as a red LED. The red light source 313 is configured to generate red light (hereinafter referred to as R light) having intensity in the red region. Specifically, the red light source 313 is configured to generate, for example, the R light having intensity in a wavelength band of 620 nm to 660 nm. The red light source 313 is also configured to start or stop light emission in accordance with a light source drive signal supplied from the light source control unit 34. The red light source 313 is also configured to perform light emission at light emission quantity in accordance with the light source drive signal supplied from the light source control unit 34.

The multiplexer 32 is configured to be able to multiplex light emitted from the light emission unit 31 and cause the multiplexed light to be incident on the light condensation lens 33.

The light condensation lens 33 is configured to condense the light incident through the multiplexer 32 and emit the condensed light to a light guide 13.

The light source control unit 34 is configured to control each light source of the light emission unit 31 based on a system control signal outputted from the processor 4.

The processor 4 includes an image pickup device drive unit 41, an image input unit 42, an image processing unit 43, a display control unit 44, an input interface (I/F) 45, and a control unit 47.

The image pickup device drive unit 41 includes, for example, a driver circuit. The image pickup device drive unit 41 is configured to generate and output an image pickup device drive signal for driving each of the image pickup devices 26A, 26B, and 26C with an exposure time and the like in accordance with control of the control unit 47.

The image input unit 42 is configured to receive an image obtained by the endoscope apparatus 2 and perform operation for switching an output destination of the received image in accordance with a system control signal outputted from the control unit 47.

The image processing unit 43 is configured to perform, in accordance with a system control signal outputted from the control unit 47, predetermined image processing on the image outputted from the image input unit 42 and output the image on which the predetermined image processing is performed to the display control unit 44.

The display control unit 44 is configured to generate, in accordance with a system control signal outputted from the control unit 47, a display image by using the image outputted from the image processing unit 43 and output the generated display image to the display apparatus 5.

The input I/F 45 includes one or more switches and/or buttons through which instruction or the like in accordance with an operation by a user such as a surgeon can be performed on the control unit 47. Specifically, the input I/F 45 includes, for example, an observation mode switching switch through which instruction for setting an observation mode when the subject is observed by the endoscope system 1A to any of a white light observation mode and a fluorescence observation mode can be performed on the control unit 47.

The control unit 47 is configured to generate and output a system control signal for performing operation in accordance with instruction performed through the input I/F 45. The control unit 47 is configured to detect, based on instruction performed through the input I/F 45, the observation mode of the endoscope system 1A set by the user, and generate and output a system control signal for performing operation in accordance with the detected observation mode. The control unit 47 is also configured to generate a system control signal for controlling the image pickup operation of each of the image pickup devices 26A, 26B, and 26C and output the system control signal to the image pickup device drive unit 41. The control unit 47 is also configured to perform operation in accordance with a fluorescence image (equivalent to an image FIB to be described later) and operation state information (to be described later), the fluorescence image being outputted from the image input unit 42 in the fluorescence observation mode, the operation state information being outputted from the treatment instrument control apparatus 62 connected through the cable 30.

Note that, in the present embodiment, for example, each component of the processor 4 may be configured as an individual electronic circuit or may be configured as a circuit block in an integrated circuit such as an FPGA (field programmable gate array). In the present embodiment, for example, the processor 4 may include at least one CPU. In the present embodiment, for example, a computer may read and execute a program stored in a storage medium such as a non-illustrated memory, thereby performing operation, processing, and the like in accordance with functions of each component of the processor 4. Thus, the processor 4 includes a processing circuit configured to operate as hardware, or a processing circuit configured to operate in accordance with a software.

The display apparatus 5 includes an LCD (liquid crystal display) or the like and is configured to be able to display a display image outputted from the processor 4 or the like.

The treatment instrument 61 is configured to be able to apply energy supplied from the treatment instrument control apparatus 62 to desired living body tissue in the subject and perform, on the desired living body tissue, various kinds of treatment by effects of thermal energy generated in accordance with the energy application. In other words, the treatment instrument 61 has functions of an energy device and is configured to be able to perform treatment on living body tissue present in the subject by generating heat through application of energy supplied from the treatment instrument control apparatus 62 to the living body tissue. As illustrated in FIG. 1, the treatment instrument 61 includes a handle unit 71, a shaft 72 attached to the handle unit 71 on a proximal end side, and a treatment unit 73 provided on a distal end side of the shaft 72. The treatment instrument 61 is connected with the treatment instrument control apparatus 62 through a cable 63 extending from the handle unit 71. The treatment unit 73 includes a pair of jaw members 73*a* and 73*b* capable of opening and closing.

The handle unit 71 includes, for example, a plurality of operation levers and is configured to be able to change opening-closing states of the jaw members 73*a* and 73*b* of the treatment unit 73 in accordance with operations of the plurality of operation levers. The handle unit 71 is provided with a switch unit 74 including one or more switches for performing, to the treatment instrument control apparatus 62, instruction in accordance with an operation by the user such as the surgeon.

The shaft 72 is formed in an elongated shape, such as a cylindrical shape, with which the shaft 72 can be inserted into the subject through a trocar installed through a body wall of the subject.

The treatment unit 73 is configured to be able to hold living body tissue between the jaw members 73*a* and 73*b*. The treatment unit 73 is also configured to be able to apply energy supplied from the treatment instrument control apparatus 62 to the living body tissue held between the jaw members 73*a* and 73*b*.

The switch unit 74 is configured to be able to perform instruction to supply energy in accordance with an operation by the user from the treatment instrument control apparatus 62 to the treatment instrument 61. The switch unit 74 is also configured to be able to perform, in accordance with an operation by the user, instruction to set a method of switching a state of energy supply to the treatment instrument 61 to any of manual switching and automatic switching.

The treatment instrument control apparatus 62 includes, for example, a power circuit for generating energy to be supplied to the treatment instrument 61, and a control circuit for performing control on the treatment instrument 61. As illustrated in FIGS. 1 and 2, the treatment instrument control apparatus 62 is connected with the control unit 47 through the cable 30 and also connected with the treatment instrument 61 through the cable 63. The treatment instrument control apparatus 62 is configured to be able to perform, for example, operation for generating energy of at least one of ultrasound used for treatment such as dissection of the living body tissue, or high-frequency current used for treatment such as coagulation of the living body tissue, and supplying the energy to the treatment instrument 61. The treatment instrument control apparatus 62 is also configured to generate, in accordance with instruction performed through the switch unit 74, operation state information indicating whether the method of switching the state of energy supply to the treatment instrument 61 is set to the manual switching or the automatic switching, and is configured to output the operation state information to the control unit 47. The treatment instrument control apparatus 62 is also configured to perform operation for supplying energy in accordance with instruction through the switch unit 74 to the treatment instrument 61 when the method of switching the state of energy supply to the treatment instrument 61 is set to the manual switching. The treatment instrument control apparatus 62 is also configured to perform operation for supplying energy to the treatment instrument 61 in accordance with a system control signal outputted from the control unit 47 when the method of switching the state of energy supply to the treatment instrument 61 is set to the automatic switching.

Subsequently, effects of the medical system 1 of the present embodiment will be described below.

For example, the user connects and powers on the components of the medical system 1 and installs a plurality of trocars through an abdominal wall of the subject, and then inserts the insertion portion 6 into a body cavity of the subject through one of the plurality of trocars and also inserts the shaft 72 (and the treatment unit 73) into the body cavity of the subject through another one of the plurality of trocars. Alternatively, for example, the user connects and powers on the components of the medical system 1, and then operates the input I/F 45 to perform instruction for setting the observation mode of the endoscope system 1A to the white light observation mode and also operates the switch unit 74 to set the method of switching the state of energy supply to the treatment instrument 61 to the automatic switching.

The treatment instrument control apparatus 62 generates, in accordance with instruction performed through the switch unit 74, operation state information indicating that the method of switching the state of energy supply to the treatment instrument 61 is set to the automatic switching, and outputs the operation state information to the control unit 47.

When having detected that the observation mode of the endoscope system 1A is set to the white light observation mode based on instruction performed through the input I/F 45, for example, the control unit 47 generates a system control signal for irradiating an object with, as illumination light, white light (hereinafter referred to as W light) obtained by mixing the B light, the G light, and the R light and outputs the system control signal to the light source control unit 34.

When the observation mode of the endoscope system 1A is set to the white light observation mode based on a system control signal outputted from the processor 4, for example, the light source control unit 34 controls the light emission unit 31 to simultaneously emit light from the blue light source 311, the green light source 312, and the red light source 313. Through such operation of the light source control unit 34, for example, an object including the living body tissue in the body cavity of the subject is irradiated with the W light supplied from the light source apparatus 3 through the illumination lens 15, return light (reflected light) generated in accordance with the irradiation of the object with the W light is incident on the dichroic prism 25 through the eyepiece lens 19, the R light included in the return light is picked up by the image pickup device 26A, the G light included in the return light is picked up by the image pickup device 26B, and the B light included in the return light is picked up by the image pickup device 26C.

The signal processing circuit 27 generates, based on an image pickup signal outputted from the image pickup device 26A, an image RIA of a red component having a pixel value in accordance with intensity of the R light included in return light emitted from the object, and outputs the generated image RIA to the image input unit 42. The signal processing circuit 27 also generates, based on an image pickup signal outputted from the image pickup device 26B, an image GIA of a green component having a pixel value in accordance with intensity of the G light included in return light emitted from the object, and outputs the generated image GIA to the image input unit 42. The signal processing circuit 27 also generates, based on an image pickup signal outputted from the image pickup device 26C, an image BIA of a blue component having a pixel value in accordance with intensity of the B light included in return light emitted from the object, and outputs the generated image BIA to the image input unit 42.

When having detected that the observation mode of the endoscope system 1A is set to the white light observation mode based on instruction performed through the input I/F 45, the control unit 47 generates a system control signal for setting an output destination of each of the images RIA, GIA, and BIA obtained by the endoscope apparatus 2 to the image processing unit 43, and outputs the system control signal to the image input unit 42.

The image processing unit 43 performs predetermined image processing on each of the images RIA, GIA, and BIA outputted from the image input unit 42 and outputs each image on which the predetermined image processing is performed to the display control unit 44.

When the observation mode of the endoscope system 1A is set to the white light observation mode, for example, the display control unit 44 generates, in accordance with a system control signal outputted from the control unit 47, a white light observation image by allocating the image RIA outputted from the image processing unit 43 to a red (R) channel of the display apparatus 5, allocating the image GIA outputted from the image processing unit 43 to a green (G) channel of the display apparatus 5, and allocating the image BIA outputted from the image processing unit 43 to a blue (B) channel of the display apparatus 5. The display control unit 44 also generates a display image including the white light observation image generated as described above and outputs the generated display image to the display apparatus 5.

The user checks the display image displayed on the display apparatus 5, disposes the distal end portion of the insertion portion 6 at a position where an image of the treatment target site in the subject can be picked up, and also disposes the treatment unit 73 of the treatment instrument 61 near the living body tissue at this treatment target. In addition, for example, the user contacts the treatment unit 73 to the treatment target site and operates the switch unit 74, thereby performing instruction for starting energy supply from the treatment instrument control apparatus 62 to the treatment instrument 61. Then, energy application from the treatment unit 73 to the treatment target site is started in accordance with such an operation by the user, and heat invasion occurs at the treatment target site in accordance with energy applied from the treatment unit 73.

For example, after having performed the instruction for starting energy supply from the treatment instrument control apparatus 62 to the treatment instrument 61, the user operates the input I/F 45 to perform instruction for setting the observation mode of the endoscope system 1A to the fluorescence observation mode.

When having detected that the observation mode of the endoscope system 1A is set to the fluorescence observation mode based on instruction performed through the input I/F 45, for example, the control unit 47 generates a system control signal for irradiating the object with the B light and the G light as illumination light in a time dividing manner (alternately) and outputs the system control signal to the light source control unit 34.

When the observation mode of the endoscope system 1A is set to the fluorescence observation mode based on a system control signal outputted from the processor 4, for example, the light source control unit 34 stops light emission from the red light source 313 and controls the light emission unit 31 to perform light emission from the blue light source 311 and the green light source 312 in a time dividing manner (alternately). Through such operation of the light source control unit 34, for example, in a duration in which the blue light source 311 performs light emission, the object including the living body tissue in the body cavity of the subject is irradiated with the B light supplied from the light source apparatus 3 through the illumination lens 15, and the F light is generated in accordance with the irradiation of the object with the B light and picked up by the image pickup device 26B. In addition, through the above-described operation of the light source control unit 34, for example, in a duration in which the green light source 312 performs light emission, the object including the living body tissue in the body cavity of the subject is irradiated with the G light supplied from the light source apparatus 3 through the illumination lens 15, and return light (reflected light of the G light) generated in accordance with the irradiation of the object with the G light is picked up by the image pickup device 26B.

The signal processing circuit 27 generates, based on an image pickup signal outputted from the image pickup device 26B, an image GIB of a green component having a pixel value in accordance with intensity of the return light emitted from the object in response to the G light and outputs the generated image GIB to the image input unit 42. In addition, the signal processing circuit 27 generates, based on an image pickup signal outputted from the image pickup device 26C, an image FIB of a green component corresponding to a fluorescence image having a pixel value in accordance with intensity of the F light emitted from the object and outputs the generated image FIB to the image input unit 42.

In other words, the endoscope apparatus 2 has functions of a fluorescence detection apparatus and is configured to be able to detect fluorescence emitted from the living body tissue on which treatment is performed by the treatment instrument 61. The endoscope apparatus 2 is also configured to output, to the processor 4, a fluorescence image obtained by performing image pickup of the fluorescence emitted from the living body tissue on which treatment is performed by the treatment instrument 61.

Note that, in the following description of the present embodiment, an image in accordance with return light (reflected light of the B light) generated by irradiating the object with the B light in the fluorescence observation mode is generated by the signal processing circuit 27 but not outputted to each component at a stage subsequent to the image input unit 42 (not used for display image generation nor the like).

When having detected that the observation mode of the endoscope system 1A is set to the fluorescence observation mode based on instruction performed through the input I/F 45, the control unit 47 sets the output destination of the image GIB obtained by the endoscope apparatus 2 to the image processing unit 43 and also generates a system control signal for setting the output destination of the image FIB obtained by the endoscope apparatus 2 to the image processing unit 43 and the control unit 47 and outputs the system control signal to the image input unit 42.

The image processing unit 43 performs predetermined image processing on each of the images GIB and FIB outputted from the image input unit 42 and outputs each image on which the predetermined image processing is performed to the display control unit 44.

When the observation mode of the endoscope system 1A is set to the fluorescence observation mode, for example, the display control unit 44 generates, in accordance with a system control signal outputted from the control unit 47, a fluorescence observation image by allocating the image GIB outputted from the image processing unit 43 to the R channel and the B channel of the display apparatus 5 and allocating the image FIB outputted from the image processing unit 43 to the G channel of the display apparatus 5. In addition, the display control unit 44 generates a display image including the fluorescence observation image generated as described above and outputs the generated display image to the display apparatus 5.

Figure 3:
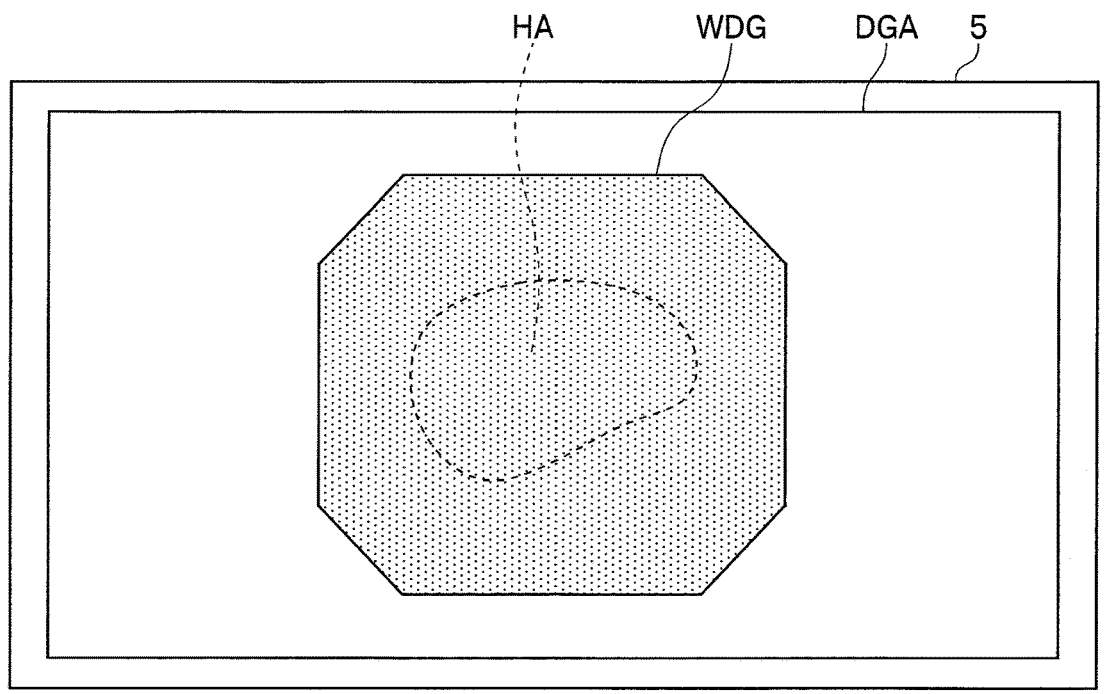
FIG. 3 is a diagram illustrating an example of a display image displayed when an observation mode of the endoscope system according to an exemplary embodiment is set to a white light observation mode.
Figure 4:
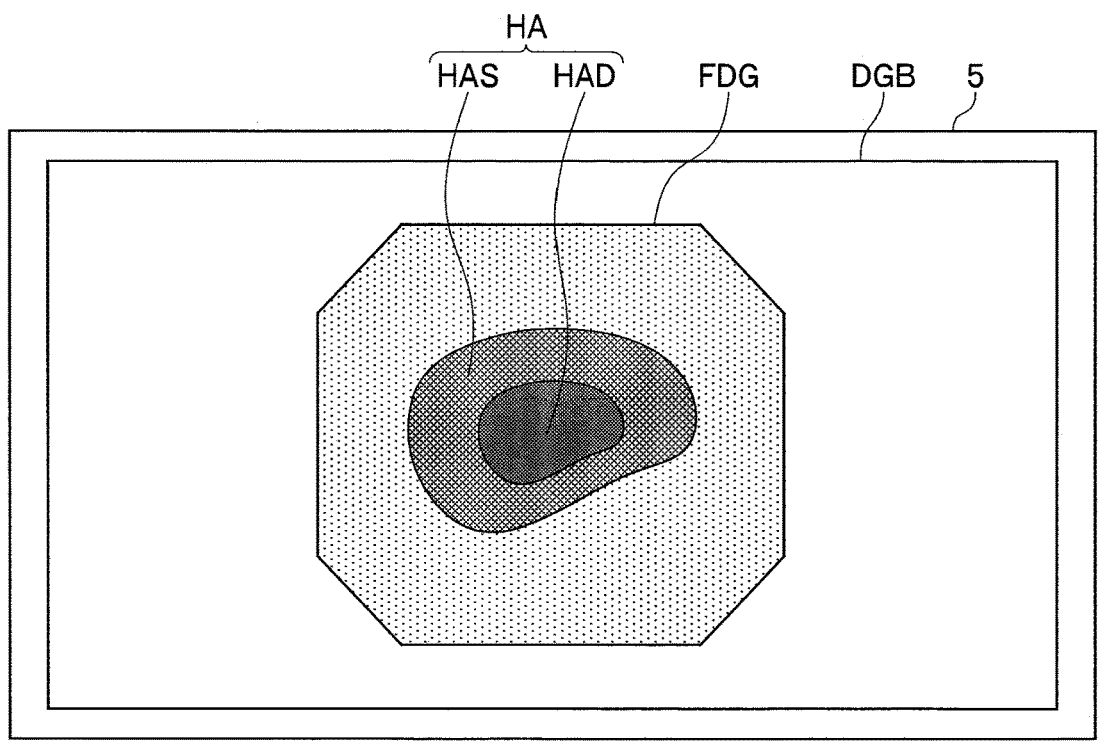
FIG. 4 is a diagram illustrating an example of the display image displayed when the observation mode of the endoscope system according to an exemplary embodiment is set to a fluorescence observation mode.

According to the above-described processing and the like, for example, a display image DGA including a white light observation image WDG as illustrated in FIG. 3 is displayed on the display apparatus 5 when the observation mode of the endoscope system 1A is set to the white light observation mode in a state in which energy application from the treatment unit 73 to the treatment target site is performed. In addition, according to the above-described processing and the like, for example, a display image DGB including a fluorescence observation image FDG as illustrated in FIG. 4 is displayed on the display apparatus 5 when the observation mode of the endoscope system 1A is set to the fluorescence observation mode in a state in which energy application from the treatment unit 73 to the treatment target site is performed.

With the white light observation image WDG in FIG. 3, it is possible to visually recognize a boundary part of a heat invasion region HA corresponding to a region suffering heat invasion at the treatment target site, but it is impossible to visually recognize the degree of heat invasion inside the heat invasion region HA. However, with the fluorescence observation image FDG in FIG. 4, it is possible to visually recognize that two regions, namely, a region HAD in which a reach depth of heat invasion is relatively deep and a region HAS in which the reach depth of heat invasion is relatively shallow, exist inside the heat invasion region HA. Note that a phenomenon or the like as a basis for visualization of the region HAD and the region HAS as exemplarily illustrated in FIG. 4 will be described later.

When having detected that the observation mode of the endoscope system 1A is set to the fluorescence observation mode based on instruction performed through the input I/F 45 and having detected that the method of switching the state of energy supply to the treatment instrument 61 is set to the automatic switching based on the operation state information outputted from the treatment instrument control apparatus 62, the control unit 47 generates and outputs a system control signal for controlling the state of energy supply to the treatment instrument 61 based on the image FIB outputted from the image input unit 42.

Figure 7:
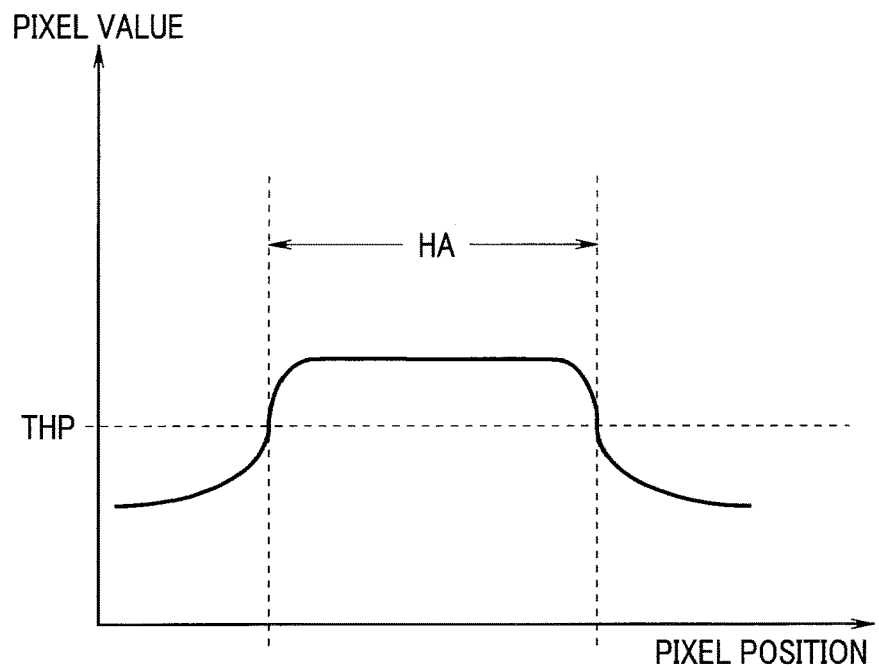
FIG. 7 is a graph illustrating an example of extracting a heat invasion region in a medical system according to the embodiment.
Figure 8:
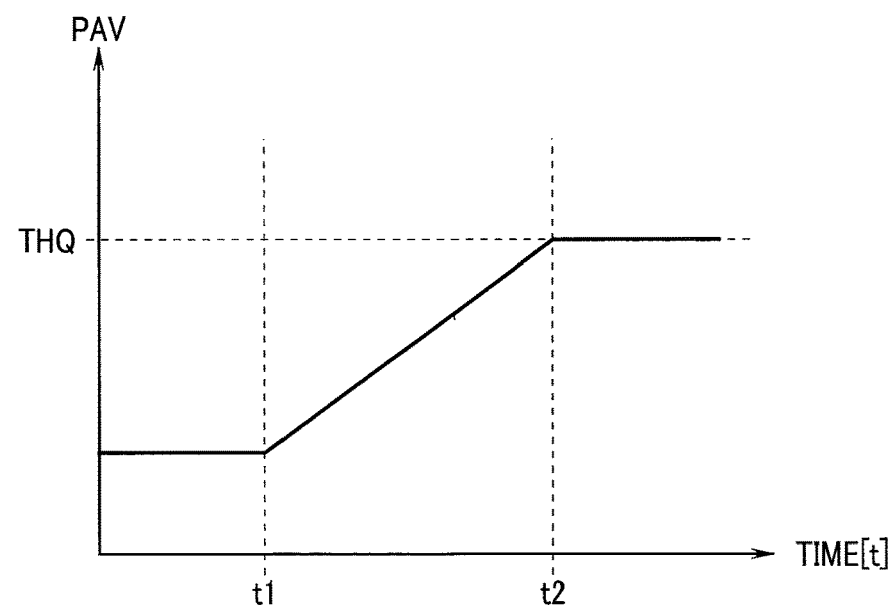
FIG. 8 is a graph illustrating an example of stopping energy supply when an average value of pixel values of pixels included in the heat invasion region exceeds a second threshold value in the medical system according to an exemplary embodiment.

FIG. 7 is a graph illustrating an example of extracting the heat invasion region HA in the medical system according to the embodiment. FIG. 8 is a graph illustrating an example of stopping energy supply when an average value PAV of pixel values of pixels included in the heat invasion region HA exceeds a second threshold value THQ in the medical system according to the embodiment. In the example in FIG. 8, heat treatment starts at time t1.

Specifically, for example, the control unit 47 extracts, as the heat invasion region HA, a region constituted by a group of pixels having a pixel value equal to or larger than a predetermined threshold value THP among pixels included in the image FIB outputted from the image input unit 42, and determines whether the average value PAV of the pixel values of pixels included in the heat invasion region HA exceeds a second threshold value THQ (>THP). Then, for example, when having acquired a determination result that the average value PAV is equal to or smaller than the second threshold value THQ, the control unit 47 generates a system control signal for continuing energy supply to the treatment instrument 61 and outputs the system control signal to the treatment instrument control apparatus 62. For example, when having acquired a determination result that the average value PAV exceeds the second threshold value THQ at time t2, the control unit 47 generates a system control signal for stopping energy supply to the treatment instrument 61 and outputs the system control signal to the treatment instrument control apparatus 62.

Figure 9:
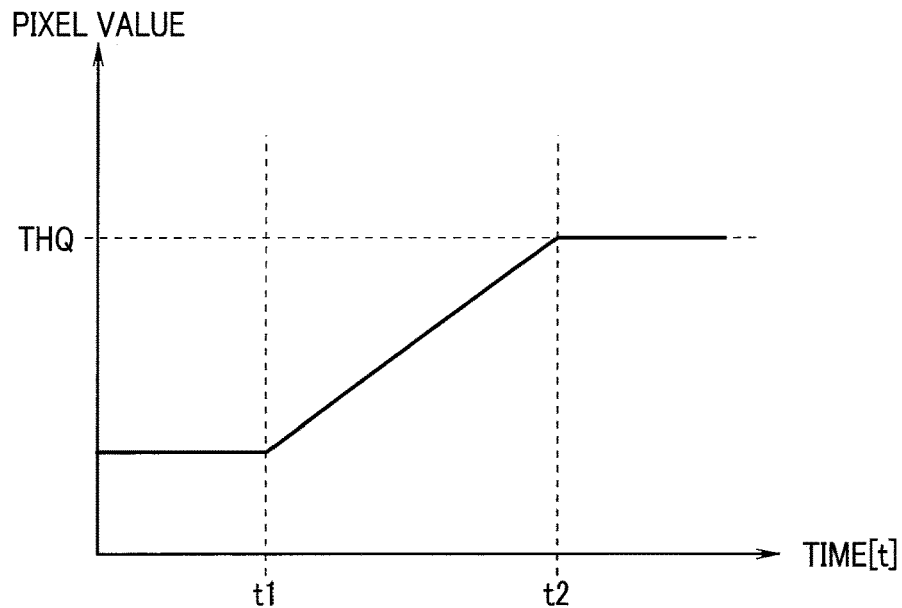
FIG. 9 is a graph illustrating an example of stopping energy supply when a pixel value of at least one pixel included in the heat invasion region exceeds the second threshold value in the medical system according to an exemplary embodiment.

FIG. 9 is a graph illustrating an example of stopping energy supply when a pixel value of at least one pixel included in the heat invasion region HA exceeds the second threshold value THQ in the medical system according to the embodiment.

In FIG. 8, the energy supply was stopped when the average value PAV of the pixel values exceeded the second threshold value THQ. However, the energy supply to the energy device may be stopped when, instead of the average value PAV, a pixel value of at least one pixel included in the heat invasion region HA exceeds the second threshold value THQ, as illustrated in FIG. 9.

Note that, in the present embodiment, the second threshold value THQ used for the above-described threshold-value determination may be a fixed value set in advance or may be a variable value set in accordance with a kind of treatment performed on the treatment target site.

In the present embodiment, for example, the control unit 47 may perform, based on a determination result of threshold-value determination in which a plurality of threshold values are used, control to reduce a supply amount of energy supplied to the treatment instrument 61 at stages whenever the average value PAV exceeds each one of the plurality of threshold values.

Figure 10:
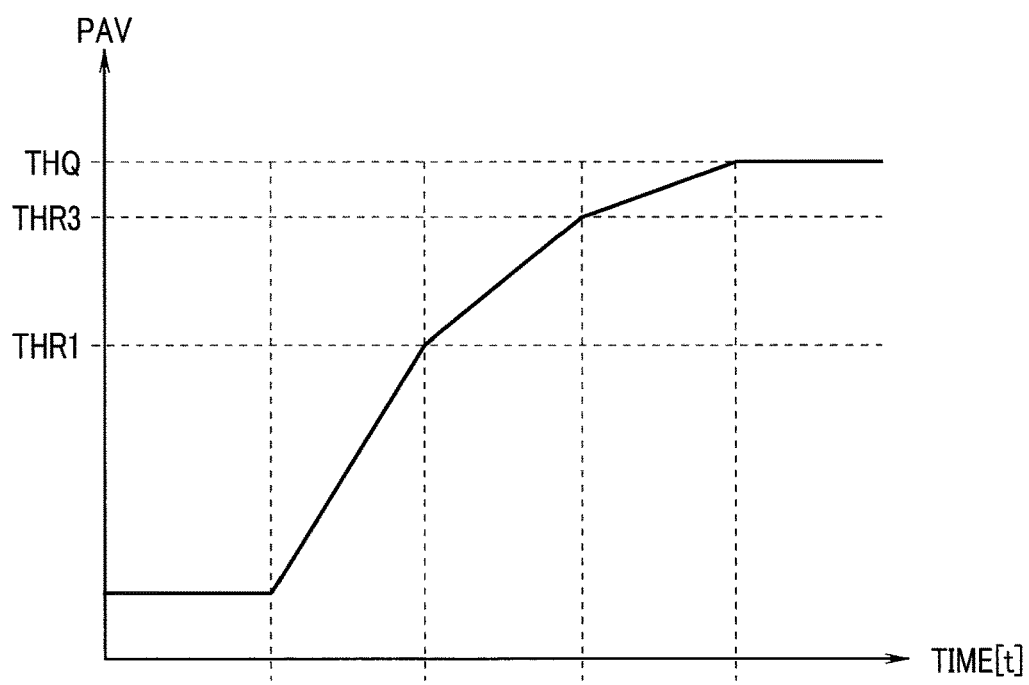
FIG. 10 is a graph illustrating an example of restricting energy supply when the average value of the pixel values of the pixels included in the heat invasion region exceeds the first threshold value, restricting energy supply more greatly when the average value exceeds a third threshold value, and stopping energy supply when the average value exceeds the second threshold value, in the medical system according to an exemplary embodiment.
Figure 11:
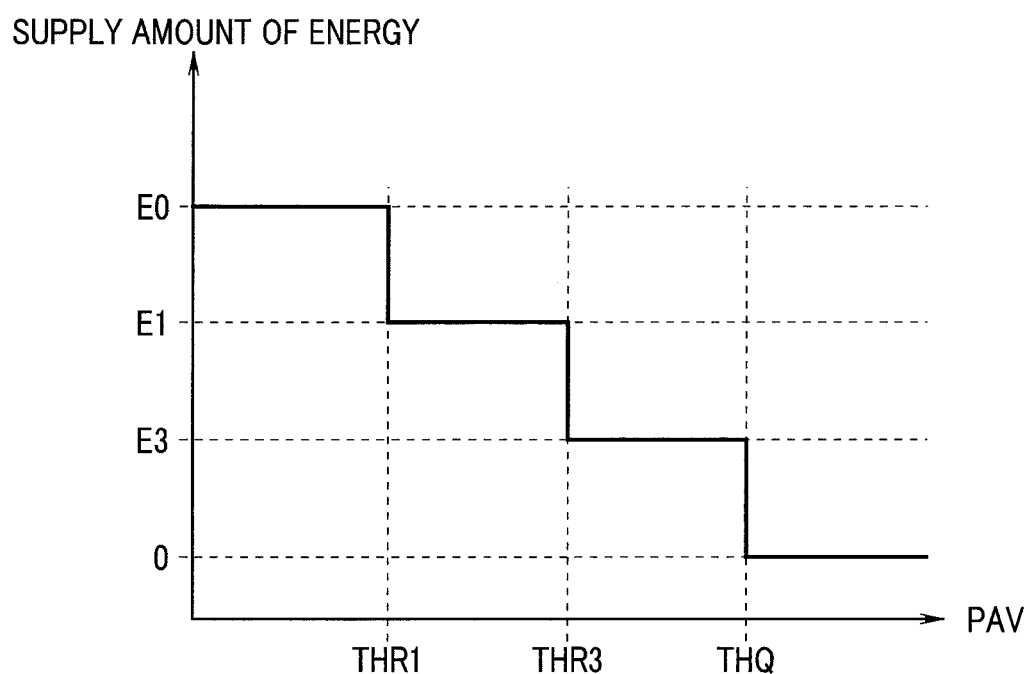
FIG. 11 is a graph illustrating an example of a supply amount of energy to an energy device, in which the supply amount of energy is varied with the first threshold value, the third threshold value, and the second threshold value as boundaries, in the medical system according to an exemplary embodiment.

FIG. 10 is a graph illustrating an example of restricting energy supply when the average value PAV of the pixel values of the pixels included in the heat invasion region HA exceeds a first threshold value THR1, restricting energy supply more greatly when the average value exceeds a third threshold value THR3, and stopping energy supply when the average value exceeds a second threshold value THQ, in the medical system according to the embodiment. FIG. 11 is a graph illustrating an example of a supply amount of energy to an energy device, in which the supply amount of energy is varied with the first threshold value THR1, the third threshold value THR3, and the second threshold value THQ as boundaries, in the medical system according to the embodiment.

For example, when having acquired a determination result that the average value PAV is equal to or smaller than the first threshold value THR1, the control unit 47 generates system control signal for continuing energy supply to the treatment instrument 61 and outputs the system control signal to the treatment instrument control apparatus 62. The first threshold value THR1 is larger than the predetermined threshold value THP and smaller than the second threshold value THQ. As a result, a supply amount of energy E0 is supplied to the energy device.

For example, when having acquired a determination result that the average value PAV exceeds the first threshold value THR1, the control unit 47 generates a system control signal for reducing energy supply to the treatment instrument 61 and outputs the system control signal to the treatment instrument control apparatus 62. As a result, the supply amount of energy to the energy device changes from E0 to E1, which is smaller than E0.

For example, when having acquired a determination result that the average value PAV exceeds the third threshold value THR3, the control unit 47 generates a system control signal for reducing energy supply to the treatment instrument 61 more greatly than when the average value PAV exceeds the first threshold value THR1, and outputs the system control signal to the treatment instrument control apparatus 62. The third threshold value THR3 is larger than the first threshold value THR1 and smaller than the second threshold value THQ. As a result, the supply amount of energy to the energy device changes from E1 to E3, which is smaller than E1.

For example, when having acquired a determination result that the average value PAV exceeds the second threshold value THQ, the control unit 47 generates a system control signal for stopping energy supply to the treatment instrument 61, and outputs the system control signal to the treatment instrument control apparatus 62. As a result, the supply amount of energy to the energy device changes from E3 to 0.

Here, the average value PAV was compared with each of the first threshold value THR1, the third threshold value THR3, and the second threshold value THQ. However, instead of the average value PAV, a pixel value of at least one pixel included in the heat invasion region HA can be compared with each of the first threshold value THR1, the third threshold value THR3, and the second threshold value THQ.

In the present embodiment, for example, the control unit 47 may perform, based on a determination result of threshold-value determination in which a maximum value PMX of the pixel values of pixels included in the heat invasion region HA is used in place of the average value PAV, control to stop energy supply to the treatment instrument 61 when the maximum value PMX exceeds the second threshold value THQ. Furthermore, the maximum value PMX of the pixel values may be compared with each of the first threshold value THR1, the third threshold value THR3, and the second threshold value THQ, as described above.

In other words, the processor 4 has functions of an energy control apparatus and is configured to control the state of energy supply to the treatment instrument 61 based on intensity of fluorescence emitted from the living body tissue on which treatment is performed by the treatment instrument 61, the intensity corresponding to intensity of fluorescence detected by the endoscope apparatus 2 (fluorescence detection apparatus). The processor 4 is also configured to perform control to stop energy supply to the treatment instrument 61 when the intensity of fluorescence detected by the endoscope apparatus 2 (fluorescence detection apparatus) exceeds a predetermined intensity. The processor 4 is also configured to extract, from the image FIB (fluorescence image), the heat invasion region HA corresponding to a region in which treatment is performed by the treatment instrument 61, and control the state of energy supply to the treatment instrument 61 based on the pixel value of each pixel included in the heat invasion region HA. The processor 4 is also configured to perform control to stop energy supply to the treatment instrument 61 when the average value of the pixel values of pixels included in the heat invasion region HA exceeds the second threshold value THQ.

The B light emitted from the blue light source 311 has functions of excitation light for generating fluorescence from the living body tissue on which treatment is performed by the treatment instrument 61.

The applicant obtained knowledge that a positive correlation is present between the reach depth of heat invasion due to energy applied by the treatment instrument 61 and the intensity of fluorescence emitted in accordance with irradiation with the B light.

According to the present embodiment, processing or the like using the above-described knowledge is performed when the observation mode of the endoscope system 1A is set to the fluorescence observation mode. Thus, according to the present embodiment, it is possible to cause the display apparatus 5 to display the fluorescence observation image FDG with which the heat invasion region HA included in the treatment target site is visually identifiable from any other region.

According to the present embodiment, processing or the like using the above-described knowledge is performed when the observation mode of the endoscope system 1A is set to the fluorescence observation mode. Thus, according to the present embodiment, it is possible to cause the display apparatus 5 to display the fluorescence observation image FDG in which the region HAD included in the heat invasion region HA is brighter than the region HAS included in the heat invasion region HA. Note that, in FIG. 4, a hatching pattern having a concentration higher than a concentration of a hatching pattern applied to the region HAS is applied to the region HAD for sake of simplicity of illustration.

According to the present embodiment, the state of energy supply to the treatment instrument 61 is controlled by the treatment instrument control apparatus 62 based on the above-described knowledge when the observation mode of the endoscope system 1A is set to the fluorescence observation mode and the method of switching the state of energy supply to the treatment instrument 61 is set to the automatic switching. Thus, according to the present embodiment, for example, it is possible to prevent occurrence of a defect attributable to excessive heat invasion in a treatment target region and appropriately adjust the reach depth of heat invasion in the treatment target region. Thus, according to the present embodiment, it is possible to appropriately adjust a state of energy application when treatment is performed on living body tissue by using the energy device.

Figure 5:
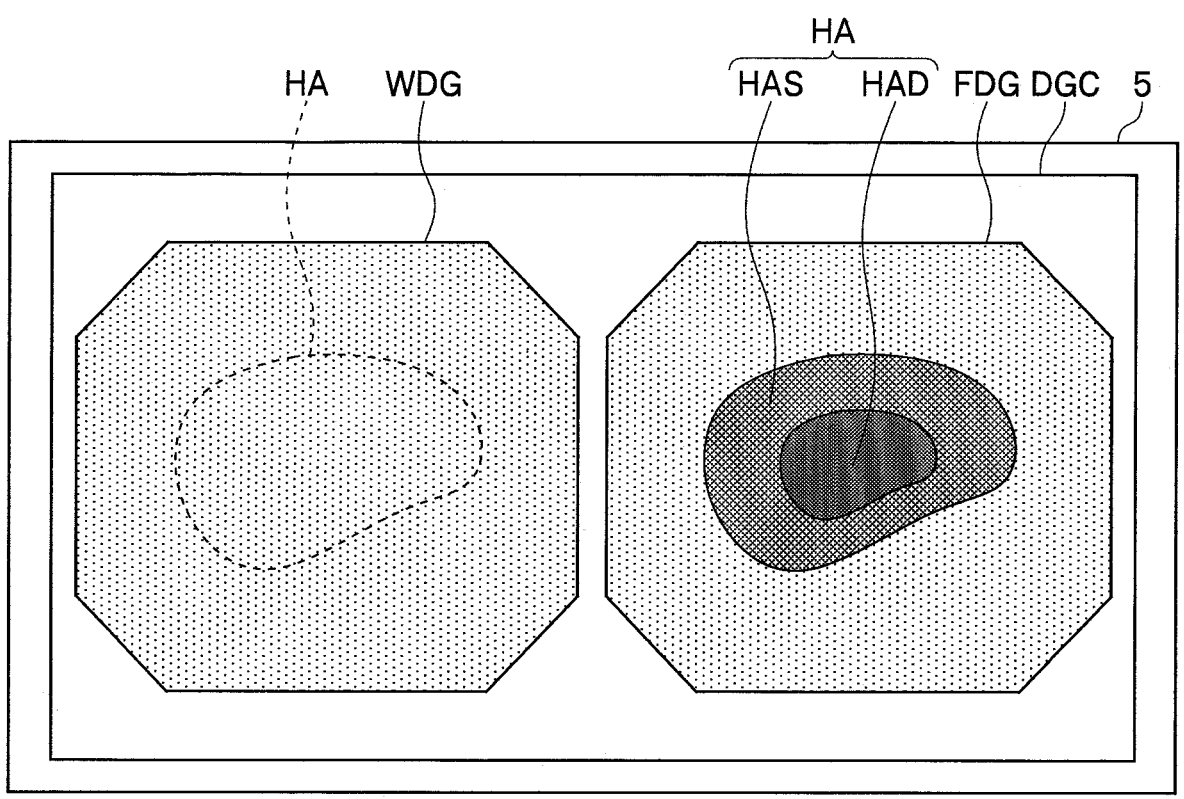
FIG. 5 is a diagram illustrating an example of the display image displayed by operation of the medical system according to an exemplary embodiment.

Note that operation of each component according to the present embodiment may be modified as appropriate to, for example, cause the display apparatus 5 to display a display image DGC including the white light observation image WDG and the fluorescence observation image FDG as illustrated in FIG. 5 when operation for irradiating an object with the W light, the B light, and the G light in a time dividing manner has been performed at the light source apparatus 3. FIG. 5 is a diagram illustrating an example of a display image displayed by operation of the medical system according to the embodiment.

The operation of each component according to the present embodiment may be modified as appropriate to, for example, cause the display apparatus 5 to display a display image in which visual information for enabling visual identification of the region HAD and the region HAS included in the heat invasion region HA detected from the image FIB is superimposed on the white light observation image WDG when operation for irradiating an object with the W light, the B light, and the G light in a time dividing manner has been performed at the light source apparatus 3.

A configuration according to the present embodiment may be modified as appropriate so that, for example, the state of energy supply to the treatment instrument 61 is controlled by the treatment instrument control apparatus 62 in place of the control unit 47. The treatment instrument control apparatus 62 may function as the energy control apparatus configured to control energy supplied to the energy device.

Figure 6:
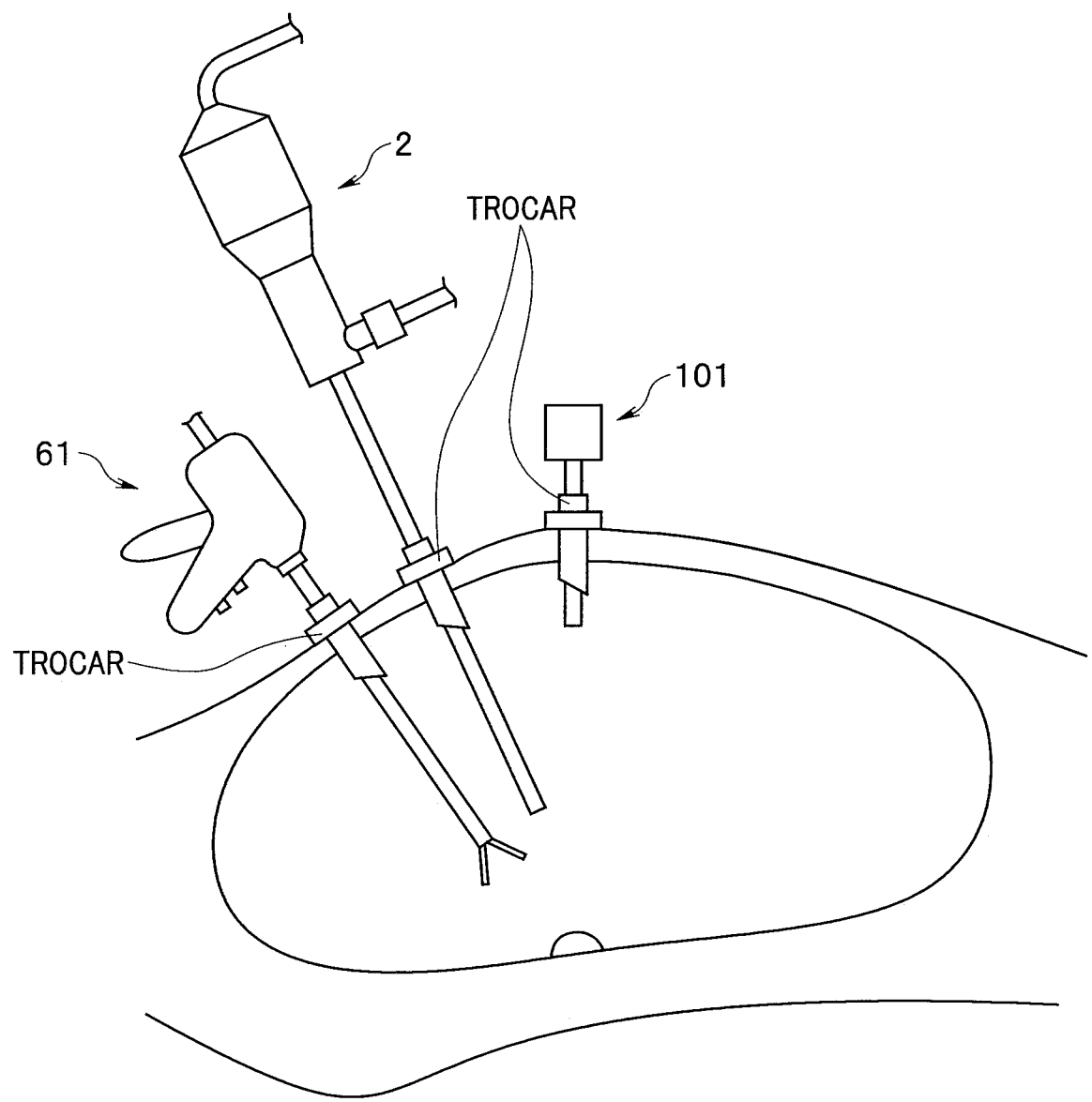
FIG. 6 is a diagram illustrating an example of a configuration when a panoramic image including a treatment target site on which treatment is performed by the medical system according to an exemplary embodiment is obtained.

A configuration according to the present embodiment may be modified as appropriate so that, for example, a panoramic camera 101 having a visual field range larger than a visual field range of the endoscope apparatus 2 is installed at a trocar as illustrated in FIG. 6, and fluorescence emitted from living body tissue on which treatment is performed by the treatment instrument 61 is picked up by the panoramic camera 101 to obtain a panoramic image. In other words, the panoramic camera 101 has functions of the fluorescence detection apparatus and is configured to be able to detect fluorescence emitted from living body tissue on which treatment is performed by the treatment instrument 61. With the above-described configuration, for example, the panoramic image obtained by the panoramic camera 101 is applicable to various usages. FIG. 6 is a diagram illustrating an example of a configuration when a panoramic image including a treatment target site at which treatment is performed by the medical system according to the embodiment is obtained.

The above-described medical system is applicable to medical fields as described below, such as surgical operation.

(1) Marking

When the above-described medical system is used, it is possible to appropriately adjust the state of energy application when marking is performed on the living body tissue by using the energy device.

(1-1) Application to Surgical Field

Application is possible to organ-targeted partial resection such as LAsTG (laparoscopy-assisted subtotal gastrectomy) or LECS (laparoscopy and endoscopy cooperative surgery). A resection site is marked by cauterization under white light observation, and then switching is made to the fluorescence observation mode. The marked site, which is a region suffering heat invasion due to cauterization, strongly emits fluorescence. Thus, the marked site can be clearly checked. Accordingly, a resection line becomes clear, and thus it is possible to perform a safer and more reliable procedure. In addition, through the marking by cauterization, it is possible to clarify a conservation line without injecting a marking drug into a target site. Note that the marking by cauterization may be performed not only on a resection region but also on a focus region of the surgeon.

Moreover, a level of energy applied to the marked site is normally different from a level of energy applied to a heat treatment site, and accordingly, a level of intensity of observed fluorescence is different between the sites. Thus, when a threshold value is provided between fluorescence intensity detected from the marked site and fluorescence intensity detected from the heat treatment site, different display colors can be set to the marked site and the heat treatment site at display of an observation image, which makes identification of the marked site easy.

(1-2) Application to Field of Digestive Organs

For example, application is possible to ESD (endoscopic submucosal dissection). Switching is made to fluorescence observation after a resection site is marked by cauterization under white light observation or when sight of the marked site is almost lost. The marked site, which is a region suffering heat invasion due to cauterization, strongly emits fluorescence. Typically, in a digestive organ procedure, a color of the marked site is not largely different from a color of living body tissue, and it is difficult to visually check the marked site. In particular, when heat invasion due to the marking is shallow, sight of a marked site is highly likely to be lost. However, when the above-described medical system is applied, it is possible to clearly check the marked site and thus more safely and more reliably perform the procedure.

Note that, in a case of a procedure in the field of digestive organs, similarly to a procedure in the surgical field, different display colors can be set to a marked site and a heat treatment site at display of an observation image, which makes identification of the marked site easier.

(2) Clarification of Presence of Cauterization/Clarification of Cauterization Range (Depth)

When the above-described medical system is used, it is possible to appropriately adjust the state of energy application and perform cauterization up to an intended level when heat treatment is provided to living body tissue by using the energy device.

(2-1) Application to Surgical Field

For example, application is possible to a posterior nasal nerve resection targeted to an allergic rhinitis patient or the like, and sweat gland resection. A resection site is cauterized under white light observation, and switching is made to fluorescence observation in a procedure to check whether hemostatic treatment of target living body tissue is reliably performed. The site, which is a region suffering heat invasion due to cauterization, emits fluorescence in accordance with a cauterization level. Typically, a state of the cauterized site is visually checked under white light observation and the cauterization level is empirically estimated by a surgeon, and thus it is difficult to determine whether a hemostatic state is appropriate. However, when the above-described medical system is applied, it is possible to clearly check the cauterization level. Accordingly, it is possible to reliably perform the hemostatic treatment and thus more safely and more reliably perform the procedure.

In the above-described resection, a dissected or resected place is clearly visualized since the treatment is performed after switching is made to fluorescence observation. It is possible to check a spreading degree of heat invasion during the treatment, and thus it is possible to conserve surrounding mucous membrane when performing cauterization and resection only on a particular nerve or cauterization target. Moreover, it is possible to observe spread of heat invasion along a living body surface by detecting a heat invasion state in fluorescence observation, and thus it is possible to control output from the energy device so that thermal spread increases at a constant speed. In addition, it is possible to observe in a procedure whether heat is uniformly applied to the target living body tissue.

The above-described medical system is also applicable to, for example, Barrett esophageal treatment. A target site is cauterized under white light observation, and switching is made to fluorescence observation in a procedure to check whether heat is uniformly applied to target living body tissue.

(2-2) Application to Urology and Gynecology Fields

For example, application is possible to TUR-BT (transurethral bladder tumor resection). A resection site is cauterized under white light observation, and switching is made to fluorescence observation in a procedure to check whether a region not emitting fluorescence (region not resected) remains in a target resection region. When the above-described medical system is applied, it is possible to clearly check any tissue not resected and thus more safely and more reliably perform the procedure.

(2-3) Application to Other Fields (such as Otorhinolaryngology, Orthopedic Surgery, and Cerebral Surgery)

The above-described fluorescence observation is applicable to, for example, cerebral surgical operation. A target site is cauterized under white light observation, switching is made to fluorescence observation in a procedure to check whether heat is uniformly applied to target living body tissue or whether hemostatic treatment is reliably performed. It is difficult to color a cauterized part in a brain and thus extremely difficult to visually check a state of a cauterized site under white light observation. When the above-described medical system is applied, it is possible to clearly check whether heat is uniformly applied to target living body tissue or clearly check the cauterization level, and thus more safely and more reliably perform the procedure.

(3) Clarification of Presence of Heat Invasion/Clarification of Heat Invasion Range (Depth)

When the above-described medical system is used, it is possible to clarify the presence of heat invasion of living body tissue by using the energy device and clarify a heat invasion range (depth).

(3-1) Application to Surgical Field

The above-described fluorescence observation is also applicable to an operative method in the surgical field. It is possible to switch the observation mode of the system from the white light observation mode to the fluorescence observation mode during and/or after an operation and check whether a nearby organ suffers heat invasion. In a case of an operative method in a situation in which an organ heat invasion of which needs to be avoided exists nearby, the observation mode can be switched from the white light observation mode to the fluorescence observation mode to check whether any adjacent organ suffers heat invasion, thereby preventing complication. For example, in a case of gastric resection, a surgeon can understand the presence of damage on an adjacent pancreas, and when invasion is checked, the surgeon can perform treatment such as attaching of a tissue adhesive seal to prevent postoperative pancreatic juice leakage.

In a case of a burn-injured patient, the observation mode can be switched to the fluorescence observation mode to visualize severity of burn. In a case of a fire or the like, some are burn-injured at bronchi or skin, and the present invention is useful for determination of necessity and an emergency degree of medical treatment on such a patient.

In a case in which a blood clot in a heart auricle (such as a left auricle) is resected, the observation mode can be switched to the fluorescence observation mode to perform fluorescence observation of a resected site so that a surgeon can check living body tissue suffering heat invasion and perform appropriate treatment (for example, fastening by a clip) when needed. As a result, it is possible to prevent complication during and/or after an operation.

In a case of an operative method using a robot or the like, when the observation mode is set to the fluorescence observation mode during an operation to prevent heat invasion of unintended living body tissue, it is possible to sense fluorescence generation and perform appropriate control output stopping, alert output to a surgeon, or the like when fluorescence is detected from the unintended living body tissue. In particular, in a case of a robot surgical operation, contact of the heated energy device, forceps, and the like with tissue is unlikely to be conveyed as a sense of the surgeon, and thus is effective. In this case, the above-described panoramic camera 101 can be used to sense fluorescence generated from tissue outside an operative visual field, and the surgeon can perform appropriate processing when fluorescence is generated.

In a case of an operative method targeted to a nearby organ such as a lung, a heart, or a pancreas, it is possible to perform fluorescence observation of an organ such as an esophagus behind the lung or the like with an endoscope or the like during or after an operation, thereby checking a state of heat invasion of the esophagus or the like. As a result, it is possible to prevent heat invasion of unintended living body tissue. Conventionally, a stapler or the like has been disposed at a nearby site to which no heat needs to be provided, but such treatment is unnecessary.

During or after an operation, the above-described medical system can be used to perform alarm output when heat invasion extends out of the operative visual field. For example, the above-described panoramic camera 101 can be used to sense fluorescence generated from tissue outside the operative visual field, and a surgeon can perform appropriate processing when fluorescence is generated. As an effect, the surgeon can focus on treatment in the operative visual field.

In a case of an operative method of calculus breakdown by a laser or the like, the observation mode can be switched to the fluorescence observation mode after calculus breakdown, thereby checking whether the vicinity of a treatment site suffers heat invasion due to the laser or the like. As a result, it is possible to assist prediction of complication during or after an operation.

In a case of a heart surgical operation, for example, ablation medical treatment (targeted to a patient of arrhythmia or the like), after an arrhythmia causing part inside a heart is resected with high-frequency current, the observation mode can be switched to the fluorescence observation mode to check whether a nearby region suffers heat invasion. As a result, it is possible to assist prediction of complication during or after an operation.

Typically, a fluorescence observation image for the above-described fluorescence observation mode is also applicable to analysis and prediction of complication during or after an operation or a prognosis by an artificial intelligence (AI) technology or the like in the surgical field. For example, it is possible to accumulate fluorescence observation image information during or after an operation and information obtained by another diagnosis apparatus (such as a CT or an MRI), analyze and estimate a state of complication during or after an operation or a state of a prognosis by using the accumulated information, produce an estimation result report, and feed the report back to the surgeon.

In the surgical field, a surgeon can introduce fluorescence image observation as an observation or check step after an operation and can clearly produce an examination record after the operation by storing a fluorescence image as the examination record.

(3-2) Application to Field of Digestive Organs

The above-described fluorescence observation is also applicable to an operative method in the field of digestive organs. During or after a surgical operation on a digestive organ, the observation mode can be switched to the fluorescence observation mode to check living body tissue suffering heat invasion, thereby checking a site at which delayed perforation potentially occurs. When living body tissue suffering heat invasion is checked, a surgeon can perform appropriate treatment when needed.

(3-3) Application to Urology and Gynecology Fields

The above-described fluorescence observation is also applicable to an operative method in the urology and gynecology fields. In the urology and gynecology fields as well, fluorescence observation can be used to perform check, alarm output, and the like for heat invasion outside the operative visual field. For example, the above-described panoramic camera 101 can be used to sense fluorescence generated from tissue outside the operative visual field, and appropriate processing can be performed when fluorescence is generated. As an effect, a surgeon can focus on treatment in the operative visual field.

In a case of an operative method using a robot or the like, when switching is made to the fluorescence observation mode during an operation to prevent heat invasion of unintended living body tissue, it is possible to sense fluorescence generation and perform appropriate control output stopping, alert output to a surgeon, and the like when fluorescence from the unintended living body tissue is detected.

In an operative method of MEA (microwave endometrial ablation) targeted to a patient of uterine myoma, uterine adenomyoma, or the like, the observation mode can be switched to the fluorescence observation mode to check living body tissue suffering heat invasion and predict complication during or after an operation.

In TUR-P (transurethral resection of prostate) as well, the observation mode can be switched to the fluorescence observation mode to check heat invasion. As a result, it is possible to assist prediction of complication during or after an operation.

(3-4) Application to Other Fields (such as Otorhinolaryngology, Orthopedic Surgery, and Cerebral Surgery)

For example, the above-described fluorescence observation is also applicable to an operative method in other fields such as otorhinolaryngology, plastic surgery, and cerebral surgery. For example, the above-described panoramic camera 101 can be used to sense fluorescence generated from tissue outside the operative visual field and check whether heat invasion extends out of the operative visual field, and a surgeon can perform appropriate processing when fluorescence is generated.

(4) Combination with Other Technologies and Apparatuses

When the above-described medical system is used in combination with another technology such as a thermography examination or with a diagnosis apparatus such as a CT or an MRI, it is possible to accumulate and analyze information obtained through examination or diagnosis by the technology or apparatus, which contributes to determination of medical treatment strategy, improvement of a procedure, or the like. For example, a fluorescence observation image during or after an operation can be analyzed in combination with information obtained by another diagnosis apparatus such as a CT or an MRI, which allows analysis and prediction of complication during or after the operation and a prognosis. In addition, an image obtained by a panoramic camera such as a lumen or abdominal cavity 360° camera can be analyzed by AI to perform overall medical treatment determination. Moreover, ICG (indocyanine green) can be locally injected into submucosa to perform treatment under fluorescence observation, thereby checking whether heat is uniformly applied to target living body tissue.

(5) Others

Fluorescence observation of the above-described medical system is also applicable to various other purposes.

A fluorescence region in a fluorescence observation image indicates a degree of heat invasion, and thus, fluorescence observation can be used to, for example, determine a healing level of thermal injury by checking a degree of the thermal injury in the fluorescence observation mode. For example, change of the healing level of the thermal injury can be detected by fluorescence observation, and a prognosis can be determined based on the change and used for determination such as meal permission. In other words, transition of change in the fluorescence observation image can be used for various kinds of determination.

With the above-described fluorescence observation, it is possible to detect tissue suffering heat invasion and thus check, for example, whether the tissue suffering heat invasion is splattered to any other region. Surgical smoke and mist are generated during an operation. A lesion such as a cancer cell included in smoke and the like potentially moves to another region and causes inflammation or the like. Thus, during or after the operation, the observation mode can be switched to the fluorescence observation mode to check scattering of the tissue suffering heat invasion.

The above-described fluorescence observation is also applicable to check of a reprocessing state after reprocessing of a reusable product such as a forceps or a treatment instrument. The fluorescence observation can be used to check whether a tissue piece provided with heat invasion adheres to, in other words, remains on the reusable product after reprocessing such as cleaning or sterilization of the reusable product. When a tissue piece provided with heat invasion adheres to the reusable product, the reusable product can be observed in the above-described fluorescence observation mode before an operation, thereby checking for the presence or a remaining state of such a tissue piece and recording an image of the state.

The above-described medical system can be used for training, education, or the like of a doctor-in-training. For example, an experienced-and-skilled doctor and a doctor-in-training apply heat to a treatment site in different manners. A fluorescence observation image can be used to quantify and visualize the manner, amount, or the like of the heat application. Thus, the above-described fluorescence observation is also applicable to training or the like of a doctor-in-training.

The above-described fluorescence observation can be also used to check whether inside of an organ is cleaned during an operation. In addition, a fluorescence image of the cleaned organ can be recorded and used to check a state of cleaning in the organ after the operation.

Note that the present invention is not limited to the above-described embodiment but may be subjected to various kinds of modifications and applications without departing from the scope of the invention. Description has been made above mainly on the case where the present invention is a medical system or a processor, for example, but the present invention may be an energy control method for performing the same processing as that performed by the medical system and the processor.

What is claimed is:
1. A medical system comprising:
a light source configured to generate excitation light; and
a processor including a memory, the processor being configured to:
control energy supplied to an energy device configured to perform heat treatment on living body tissue;
generate a fluorescence image based on an image pickup signal obtained by imaging the living body tissue irradiated with the excitation light;
output a control signal configured to restrict energy supply to the energy device when a pixel value of at least one pixel among a plurality of pixels included in the fluorescence image exceeds a first threshold value;
acquire operation state information in accordance with an input from a user, the operation state information indicating whether a method of switching a state of energy supply to the energy device is set to a manual switching or an automatic switching.

2. The medical system according to claim 1, wherein the processor is configured to output the control signal configured to stop energy supply to the energy device when the pixel value of the at least one pixel among the plurality of pixels included in the fluorescence image exceeds a second threshold value larger than the first threshold value.

3. The medical system according to claim 1, wherein
the processor is configured to:
  extract a heat invasion region that includes a group of pixels having a pixel value that exceeds a predetermined threshold value smaller than the first threshold value among the plurality of pixels included in the fluorescence image;
  determine whether a pixel value of each of pixels included in the heat invasion region exceeds the first threshold value; and
  output the control signal configured to restrict energy supply to the energy device when the pixel value of each of the pixels included in the heat invasion region is determined to exceed the first threshold value.

4. The medical system according to claim 3, wherein the processor is configured to:
  calculate an average value of pixel values of the plurality of pixels included in the heat invasion region;
  determine whether the average value exceeds the first threshold value; and
  output the control signal configured to restrict energy supply to the energy device when the average value is determined to exceed the first threshold value.

5. The medical system according to claim 3, further comprising:
  an endoscope configured to pick up an image of the fluorescence emitted from the living body tissue on which the heat treatment is performed by the energy device; and
  a camera configured to image, in a visual field range larger than a visual field range of the endoscope, the fluorescence emitted from the living body tissue on which the heat treatment is performed by the energy device.

6. The medical system according to claim 1, wherein
  the light source is configured to emit in an alternating manner between the excitation light and a white light, and
  the processor is configured to:
    generate a white light image based on an image pickup signal obtained by imaging the living body tissue irradiated with the white light, and
    cause a display to display a display image including the fluorescence image and the white light image.

7. The medical system according to claim 1, wherein the processor includes a processor and a control circuit.

8. The medical system according to claim 7, wherein the control circuit is configured to output the control signal configured to restrict energy supply to the energy device and acquire the operation state information.

9. The medical system according to claim 7, wherein the processor is configured to control energy supplied to the energy device and generate the fluorescence image.

10. The medical system according to claim 1, wherein the processor is configured to control the energy supply to decrease without stopping energy supply to the energy device.

11. An energy control method comprising:
  generating a fluorescence image based on an image pickup signal obtained by imaging living body tissue irradiated with excitation light;
  outputting a control signal configured to restrict energy supply to an energy device when a pixel value of at least one pixel among a plurality of pixels included in the fluorescence image exceeds a first threshold value; and
  acquiring operation state information in accordance with an input from a user, the operation state information indicating whether a method of switching a state of energy supply to the energy device is set to a manual switching or an automatic switching.

12. The energy control method according to claim 11, further comprising:
  extracting a region that includes a group of pixels having a pixel value that exceeds a predetermined threshold value smaller than the first threshold value among the plurality of pixels included in the fluorescence image, as a heat invasion region;
  determining whether a pixel value of each of pixels included in the heat invasion region exceeds the first threshold value; and
  outputting the control signal configured to restrict energy supply to the energy device when the pixel value of each of the pixels included in the heat invasion region is determined to exceed the first threshold value.

13. A processor comprising a processing circuit, the processing circuit being configured to:
  generate a fluorescence image based on an image pickup signal obtained by imaging living body tissue irradiated with excitation light;
  generate a control signal configured to restrict energy supply to an energy device and output the control signal to an energy control apparatus when a pixel value of at least one pixel among a plurality of pixels included in the fluorescence image exceeds a first threshold value; and
  acquire operation state information in accordance with an input from a user, the operation state information indicating whether a method of switching a state of energy supply to the energy device is set to a manual switching or an automatic switching.

14. The processor according to claim 13, wherein the fluorescence image has a pixel value in accordance with intensity of fluorescence emitted from the living body tissue.

15. The processor according to claim 14, wherein the processing circuit is configured to extract a region that includes a group of pixels having a pixel value that exceeds a predetermined threshold value smaller than the first threshold value among the plurality of pixels included in the fluorescence image, as a heat invasion region.

16. The processor according to claim 15, wherein the processing circuit is configured to:
  calculate an average value of pixel values of the plurality of pixels included in the heat invasion region; and
  determine whether the average value exceeds the first threshold value.

17. The processor according to claim 16, wherein
the processing circuit is configured to generate the control signal configured to continue energy supply to the energy device and output the control signal to the energy control apparatus when the average value is determined to be equal to or smaller than the first threshold value.

18. The processor according to claim 17, wherein
the processing circuit is configured to generate the control signal configured to restrict energy supply to the energy device and output the control signal to the energy control apparatus when the average value is determined to exceed the first threshold value.

19. The processor according to claim 18, wherein the processing circuit is configured to:
when the average value is determined to exceed a third threshold value larger than the first threshold value and smaller than a second threshold value, generate the control signal configured to restrict energy supply to the energy device more greatly than when the average value is determined to exceed the first threshold value and output the control signal to the energy control apparatus.

20. The processor according to claim 18, wherein the processing circuit is configured to generate the control signal configured to stop energy supply to the energy device and output the control signal to the energy control apparatus when the average value is determined to exceed a second threshold value.

21. The processor according to claim 15, wherein the processing circuit is configured to:
calculate a maximum value of the pixel values of the plurality of pixels included in the heat invasion region; and
generate the control signal configured to stop energy supply to the energy device and output the control signal to the energy control apparatus when the maximum value exceeds a second threshold value.

22. The processor according to claim 13, wherein the processing circuit is configured to output the control signal to the energy control apparatus when the method of switching the state of energy supply to the energy device is set to the automatic switching.

23. The processor according to claim 13, wherein the processing circuit is configured to:
cause a light source apparatus to emit in an alternating manner between the excitation light and a white light; and
generate a white light image based on an image pickup signal obtained by imaging the living body tissue irradiated with the white light.

24. The processor according to claim 23, wherein the processing circuit is configured to:
extract a heat invasion region constituted by a group of pixels having a pixel value that exceeds a predetermined threshold value among the plurality of pixels included in the fluorescence image; and
superimpose information on a boundary part of the heat invasion region on the white light image.

25. The processor according to claim 24, wherein the processing circuit is configured to extract a first region and a second region in the heat invasion region, the first region having a heat invasion depth that is deeper than a heat invasion depth of the second region.

26. The processor according to claim 25, wherein the processing circuit is configured to superimpose, on the white light image, visual information for enabling visual identification of the first region and the second region.

27. The processor according to claim 26, wherein the processing circuit is configured to extract, as the first region, a region of fluorescence detected from a marked site, and extract, as the second region, a region of fluorescence detected from a heat treatment site.

* * * * *